US007407633B2

(12) United States Patent
Potember et al.

(10) Patent No.: US 7,407,633 B2
(45) Date of Patent: Aug. 5, 2008

(54) METHOD AND APPARATUS FOR AIR TREATMENT

(75) Inventors: Richard S. Potember, Dayton, MD (US); Wayne A. Bryden, Ellicott City, MD (US)

(73) Assignee: The Johns Hopkins University, Baltimore, MD (US)

(*) Notice: Subject to any disclaimer, the term of this patent is extended or adjusted under 35 U.S.C. 154(b) by 438 days.

(21) Appl. No.: 10/257,196

(22) PCT Filed: Feb. 26, 2002

(86) PCT No.: PCT/US02/05742

§ 371 (c)(1), (2), (4) Date: Oct. 9, 2002

(87) PCT Pub. No.: WO03/028773

PCT Pub. Date: Apr. 10, 2003

(65) Prior Publication Data

US 2004/0120845 A1 Jun. 24, 2004

Related U.S. Application Data

(60) Provisional application No. 60/327,192, filed on Oct. 4, 2001.

(51) Int. Cl.
*A61L 9/00* (2006.01)

(52) U.S. Cl. .................. 422/121; 422/120; 422/186.07

(58) Field of Classification Search ................. 422/120, 422/121, 186.07
See application file for complete search history.

(56) References Cited

U.S. PATENT DOCUMENTS

| | | | | |
|---|---|---|---|---|
| 4,863,687 | A | 9/1989 | Stevens et al. | |
| 4,865,749 | A | 9/1989 | Yoshida | |
| 5,145,822 | A * | 9/1992 | Falke et al. | 502/150 |

(Continued)

FOREIGN PATENT DOCUMENTS

| | | | |
|---|---|---|---|
| CH | 650940 | A5 * | 8/1985 |

(Continued)

*Primary Examiner*—Jill Warden
*Assistant Examiner*—Sean E. Conley
(74) *Attorney, Agent, or Firm*—Francis A. Cooch

(57) ABSTRACT

A method and apparatus is described for neutralizing airborne pathogens in ventilated air, and in heating or air conditioning systems. The pathogen neutralization system is effective against a wide spectrum of pathogens, it incorporates commercially available components, and it can be readily integrated into commercial HVAC systems where it neutralizes airborne pathogens in large volumes of ventilated air in real time without any chemical reagents. Typically, the system has a flow-through reaction chamber that contains a UV light source that emits short intense flashes of broad-spectrum UV light, a source of water vapor or spray, and an ozone generator. The system generates highly reactive ozone intermediates by irradiating ozone gas with UV light in the presence of water droplets or water vapor. The pathogens that can be neutralized by this system include bacteria, viruses, spores, fungi and parasites.

22 Claims, 12 Drawing Sheets

U.S. PATENT DOCUMENTS 5,186,903 A * 2/1993 Cornwell .................... 422/122
5,614,151 A * 3/1997 LeVay et al. .................. 422/24
5,656,242 A * 8/1997 Morrow et al. ................ 96/224
5,853,457 A * 12/1998 Eysmondt et al. ............. 95/138
5,997,619 A * 12/1999 Knuth et al. .................. 96/224
6,144,175 A * 11/2000 Parra .......................... 315/307
6,165,423 A * 12/2000 Crosbie ................. 422/186.07
6,171,548 B1 * 1/2001 Rose et al. .................... 422/20
6,214,303 B1 * 4/2001 Hoke et al. ................. 423/210
6,287,465 B1 9/2001 Watanabe et al.
6,589,486 B1 * 7/2003 Spanton ...................... 422/121
2003/0056648 A1 * 3/2003 Fornai et al. ................... 95/65
2003/0155228 A1 * 8/2003 Mills et al. ............... 204/157.3
2004/0005252 A1 1/2004 Siess

FOREIGN PATENT DOCUMENTS

DE 36 28 030 A1 2/1988
DE 43 36 717 A1 5/1995
JP 10296044 11/1998
WO WO 01/39868 A1 6/2001

* cited by examiner

POROUS MATRIX
DUOCEL® ALUMINUM METAL FOAM
6-8 %, 6101-O ALLOY

10 PPI 20 PPI 40 PPI

SYSTEM INLET
*Erwinia herbicola*
Background Measurements (Fan Only)

SYSTEM OUTLET
*Erwinia herbicola*
Background Measurements (Fan Only)

SYSTEM OUTLET
*Erwinia herbicola*
Neutralization System Off (Fan Only)

SYSTEM INLET
*Erwinia herbicola*
Neutralization System Off (Fan Only)

SYSTEM INLET

*Erwinia herbicola*

Neutralization System Off (Water on, Fan On)

SYSTEM OUTLET

*Erwinia herbicola*

Neutralization System Off (Water on, Fan On)

SYSTEM INLET
*Erwinia herbicola*
Neutralization System Activated

SYSTEM OUTLET
*Erwinia herbicola*
Neutralization System Off Activated

SYSTEM INLET
*Bacillus Globii* Spores
Background Measurements (Fan Only)

SYSTEM OUTLET
*Bacillus Globii* Spores
Background measurements (Fan Only)

SYSTEM INLET
*Bacillus Globii* Spores
Neutralization System Off (Fan Only)

SYSTEM OUTLET
*Bacillus Globii* Spores
Neutralization System Off (Fan Only)

SYSTEM INLET
*Bacillus Globii* Spores
Neutralization System Off (Water on, Fan On)

SYSTEM OUTLET
*Bacillus Globii* Spores
Neutralization System Off (Water on, Fan On)

SYSTEM INLET
*Bacillus Globii* Spores
Neutralization System Activated

SYSTEM OUTLET
*Bacillus Globii* Spores
Neutralization System Activated

METHOD AND APPARATUS FOR AIR TREATMENT

CROSS-REFERENCE TO RELATED APPLICATION

This application claims the benefit of prior filed co-pending U.S. Provisional Application Ser. No. 60/327,192, filed Oct. 4, 2001, which is incorporated herein by reference.

BACKGROUND OF THE INVENTION

1. Field of the Invention

The present invention relates to a new, safe, effective method to neutralize or destroy a wide range of airborne pathogens (spores, bacteria and viruses) in commercial HVAC air handling systems.

2. Description of the Related Art

It is critical to develop rapid, effective, and safe (nontoxic and noncorrosive) pathogen neutralization technologies to protect civilian and military facilities from a chemical or biological attack. Within this area, emphasis is on the pathogen neutralization of domed stadiums, subways, and enclosed facilities (buildings and command centers that may contain extremely sensitive equipment. This effort is a key to eliminate the threat of biological weapons in the planning and conduct of US military operations. While no defense can stop an adversary from unleashing biological weapons, a sufficiently robust array of pathogen defenses and countermeasures-deterrents will reduce the damage resulting from biological weapons used in a particular operation.

There is also a great need to remove airborne pathogens form air handling systems in hospitals where the transmission of respiratory infections in indoor environments represents a major public health concern for which engineering alternatives are limited. Evidence for the dissemination of respiratory diseases inside buildings, and specifically by ventilation systems, exists in the epidemiological data. The risk to patients of becoming infected with *Staphylococcus*, one of the most common and deadly infections associated with prolonged hospital stay, is significant.

To accomplish these goals, a pathogen neutralization technology is needed that can destroy a wide range of pathogens (spores, bacteria, and viruses) in air in real time as it moves through an HVAC system without introducing contamination into the air handling system. The neutralization system of airborne biological pathogens is a very difficult problem to solve because many of the agents are highly resistant to traditional neutralization methods that have thus far been primarily useful to disinfect surfaces. Therefore, an aggressive neutralization approach is required.

Ozone is a highly effective disinfectant in water and on surfaces, but the use of ozone as a disinfectant to neutralize pathogens in air has not been demonstrated before. Ozone is the second most powerful oxidant and sterilant (fluorine is first) used in the destruction of bacteria and viruses. The threshold concentration at which ozone inactivates viruses and bacteria in water is low.

Ozone gas is extremely effective for controlling bacteria and virus contamination. It has been used quite successfully and safely in Europe for the purification of drinking and recreational water since the 1800's. It is fast becoming a replacement for chlorine and bromine, which have been shown to be carcinogenic. However, to date, no commercial HVAC system have been developed that uses ozone to disinfect airborne pathogens.

Ultraviolet (UV) light is reemerging as an alternative disinfectant to chlorination because of concern over toxic chemical byproducts. UV radiation treatment is unique in its mode of action, in that it does not necessarily kill the target microorganism. Instead, the UV radiation damages the DNA in the pathogen so that it cannot reproduce. Treating water with ozone bubbling through it, followed by UV irradiation (U.S. Pat. Nos. 4,156,652, 652, 4,179,616, 4,204, 4,230,571) has been shown to be an effective method of neutralizing waterborne pathogens. However, all of these systems depend on dissolving ozone in water to destroy the pathogens. The ozone intermediate free radicals formed by the interaction of ozone with water in the presence of UV light, act as oxidants on cell walls even before they penetrate inside the microorganisms where they oxidize essential components such as enzymes and proteins.

It has been reported that ozone itself does not react significantly with either water or air in the absence of UV irradiation. Water and air merely provide the medium in which ozone diffuses to react with organic molecules such as those on the outside of the pathogens in the cell wall. UV irradiation causes ozone to react with water and to decompose into various highly active and very short-lived free radicals, such as the hydroxyl radical. Theoretical and empirical evidence suggests that it is the interaction of the pathogen with the free radicals, and not with the ozone itself that is responsible for most pathogen neutralization. NIST Report "Photoinitiated Ozone-Water Reaction", J. Res. NIST, 97:499 (1992).

So far there is no effective way to disinfect or neutralize airborne pathogens in large volumes of contaminated air in real time to protect citizens against a terrorist attack using biological weapons, or to disinfect air in hospitals. The present invention provides such an apparatus and method for neutralizing airborne pathogens.

SUMMARY OF THE INVENTION

The present inventions provide an apparatus and methods for neutralizing airborne pathogens in large volumes of ventilated air in real time, which is effective against airborne pathogenic bacteria, spores and viruses. The technology is based on the formation of highly reactive ozone intermediates that form when ozone reacts with water vapor in the presence of ultraviolet light inside a flow-through reaction chamber into which contaminated room air is introduced. The highly active free radical ozone intermediates react with the pathogens in the air to neutralize them, thereby disinfecting the air. The pathogen neutralization system of the present invention can be easily installed in commercial and residential HVAC air handling systems and it uses commercially available components.

In one embodiment, the pathogen neutralization system includes a flow-through reaction chamber that has a chamber air inlet located at a first end of the reaction chamber to admit pathogen-contaminated air, and a chamber air outlet located at a second end of the reaction chamber to release pathogen-neutralized air. Between the chamber air inlet and outlet, the chamber defines a passageway for the passage of air through the chamber. Inside the reaction chamber are the following elements: an ozone generator; a water supply line; and an ultraviolet light source. In another embodiment the ozone generator is located outside the chamber. The water supply line can be hooked up to an external water reservoir located in the building that houses the neutralization system. In another embodiment, there is an external mixing chamber connected to an external water reservoir and an external ozone generator for producing a mixture of ozone and water that is then introduced as mist into the chamber through a nozzle disposed inside the chamber. In one embodiment the porous matrix is made of metal foam. The pathogen neutralization system can also include a solid support coated with one or more ozone removal catalysts.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

A method and apparatus is described for neutralizing airborne pathogens in ventilated air and in heating or air conditioning systems that circulate potentially contaminated air through air ducts. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

So far there is no known system for neutralizing airborne pathogens. Furthermore, to be practical and useful against a terrorist attack or in an building infected with pathogens, the system must be able to disinfect contaminated air in real time. The present inventions relate to an efficient, simple pathogen neutralization system that neutralizes a wide spectrum of airborne pathogens, in large volumes of ventilated air entering or leaving buildings or other enclosures through air handling systems in real time. Embodiments of the present invention require no chemical reagents, incorporate commercially available components, and can be readily integrated into commercial HVAC systems.

Figure 3:
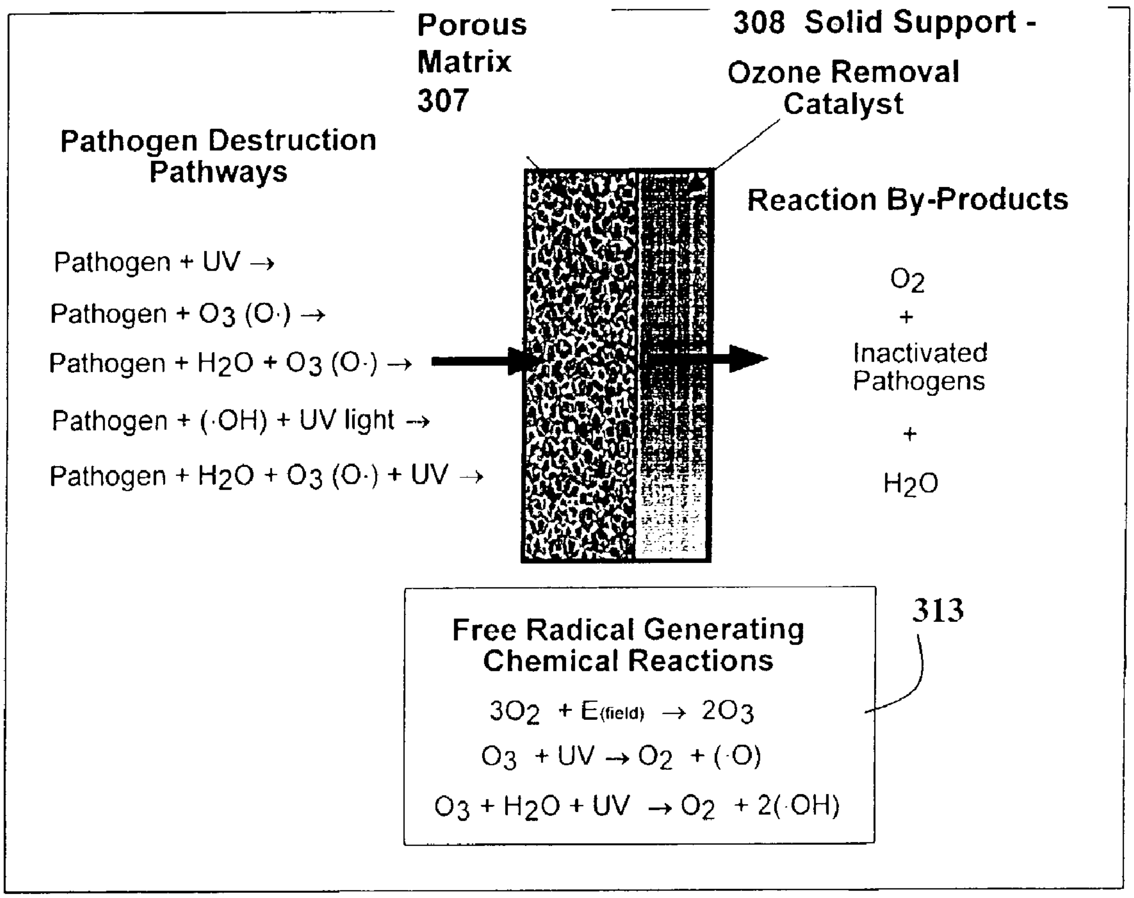
FIG. 3 illustrates the reaction pathways leading to destruction of airborne pathogens.
Figure 4:
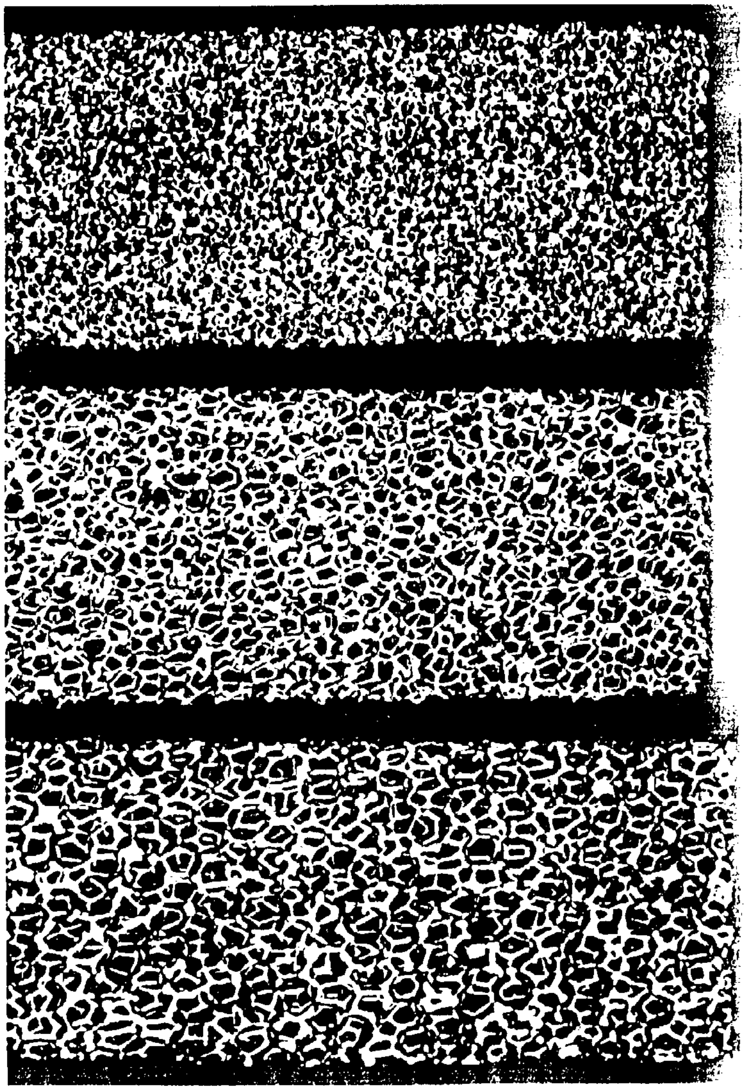
FIG. 4. Photographs of DUCOCEL® aluminum metal foam samples having densities of 6-8%, and 10 PPI (4*a*), 20 PPI (4*b*) and 40 PPI (4*c*).

The embodiments of the pathogen neutralization system and related methods rely on generating highly reactive ozone intermediates by irradiating ozone gas with high intensity, broad spectrum UV light in the presence of water droplets or water vapor inside the flow-through reaction chamber (hereinafter "the reaction chamber"). The short-lived free radicals are reported to be more effective at neutralizing pathogens than ozone or UV light alone, and they are thought to destroy a broader spectrum of airborne infectious agents. The chemical formation of these highly reactive species, indicated by the parenthetically enclosed symbols, is shown by the boxed equations 313 at the bottom of FIG. 3. Ozone gas and ultraviolet light which themselves have intrinsic anti-microbial activity are also present in the reaction chamber where they contribute to pathogen neutralization.

Figure 2:
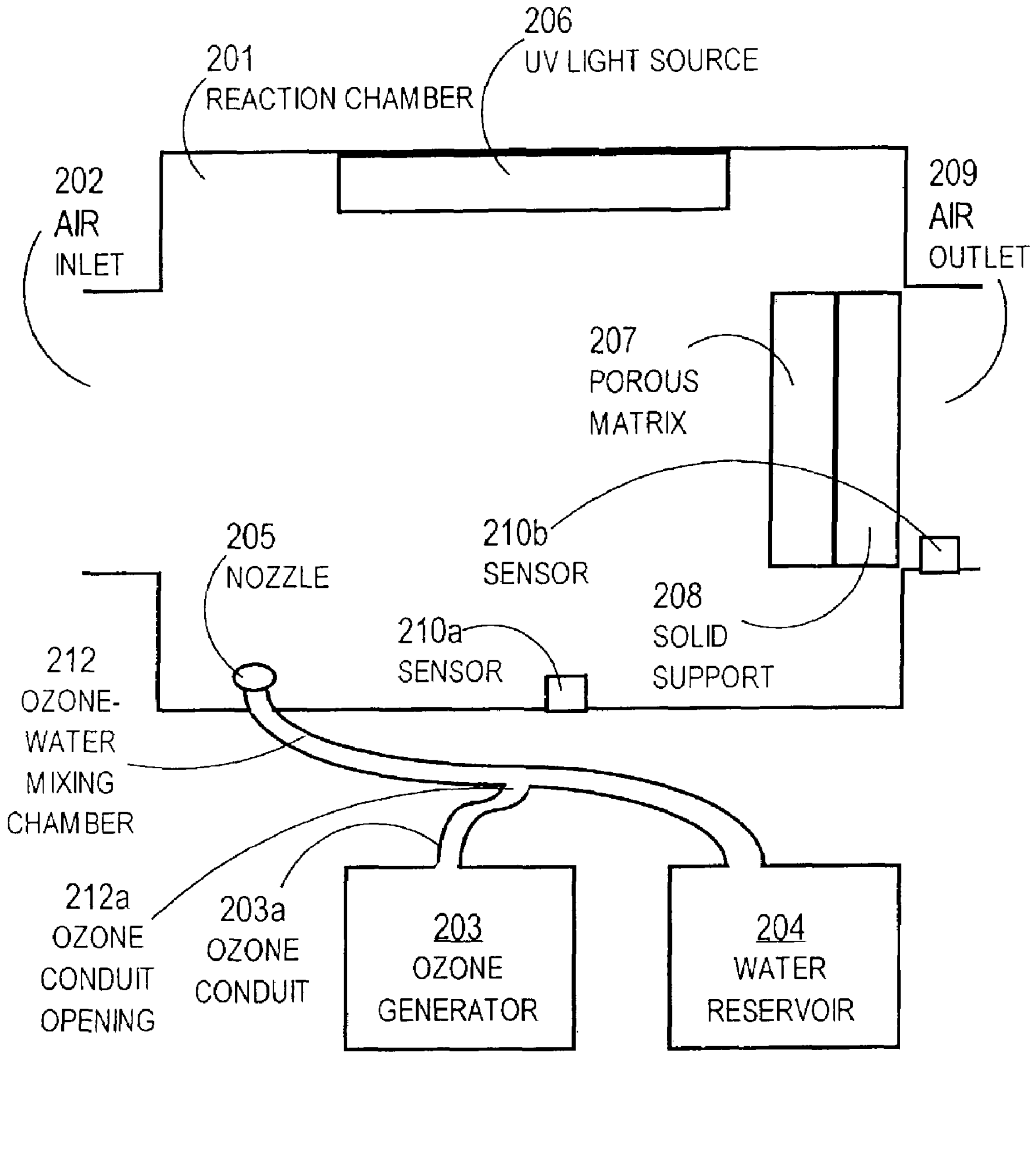
FIG. 2 is a block diagram of an embodiment of the UV/ozone pathogen neutralization system with the ozone generator 203 and the water reservoir 204 located outside the system.

The present neutralization system in its most basic form, has a reaction chamber 100 with a chamber air inlet to admit potentially pathogen-contaminated air, and a chamber air outlet 109 to release air after any airborne pathogens have been neutralized (hereinafter "pathogen-neutralized air"). Pathogen-neutralized air means air in which the pathogens have been neutralized, inactivated, mutated or killed so that they can no longer reproduce or cause infection. The pathogens that can be neutralized by this system include bacteria, viruses, spores, fungi and parasites. The neutralization system further contains a water supply line going into the reaction chamber from a water reservoir, and an ozone generator 103. A porous matrix 107 that provides additional surface area on which the neutralization of pathogens can occur, and a solid support 108 coated with ozone removal catalysts, can be added to the neutralization system. In some embodiments described in more detail below, the ozone gas and water are mixed together in a mixing chamber before being sprayed into the reaction chamber. FIG. 2**.

Broad-spectrum ultraviolet light ranging from about 100 to 350 nm causes ozone and water to react forming highly reactive ozone free radical intermediates that in turn react with and neutralize airborne pathogens. In an embodiment, an optional solid porous matrix is disposed in the system inside the reaction chamber to increase the surface area on which the ozone intermediates and pathogens can react, and to increase residence time in the reaction chamber to facilitate pathogen neutralization.

The destructive action of ozone dissolved in water on microorganisms is known, particularly on the *Escherichia coli* (*E. Coli*), *Cryptospondium, Poliovirus* and *Giardia* cysts (including *Giardia muris* and *Giardia lamblia*). E. Katzenelson and H. I. Shuval, "*Studies on the disinfection of water by ozone: viruses and bacteria*", First International Symposium on Ozone for Water & Wastewater Treatment, Vol. 1, Rice, R. G., and Browning, M. E., Eds., Hampson Press, Washington D.C. (1973); W. T. Broadwater, R. C. Hoehn, and P. H. King, "*Sensitivity of three selected bacterial species to ozone*", Appl. Microb. 26:391-393 (1973). In a moist environment, ozone reacts with water vapor to form temporary intermediate breakdown products that act as oxidants on the constituent elements of cell walls before penetrating inside microorganisms where they oxidize certain essential components (e.g., enzymes, proteins, etc.). When a large part of the membrane barrier is destroyed, the cells will lyse (unbind) resulting in immediate destruction. In a somewhat similar manner, viruses and spores are also destroyed. It has been reported that the threshold for *E. coli* neutralization lies between 0.1 and 0.2 ppm ozone.

In a study aimed at neutralizing pathogens on surfaces, it was shown that ozone gas in the presence of water vapor neutralizes cultured *E. coli* and *Staphylococcus aureus* bacteria on the surface of a petri dish. However, this experiment was conducted in a closed system where ozone was present in concentrations from between 300 and 1500 ppm and exposure times were from 10-480 seconds in duration. Only pathogens on a solid surface were neutralized. These conditions therefore do not simulate a situation such as biological warfare where airborne pathogens have been released into a room or a building. Moreover, pathogen neutralization was not achieved in real time, the chamber contained a small volume of stagnant air, and the ozone concentrations were very high. J. Kowalski, W. P. Bahnfleth, and T. S. Whittam, *Bactericidal Effects of High Airborne Ozone Concentrations on Escherichia coli and Staphylococcus aureus*, Ozone Science & Engineering 20:205-221 (1998). The authors suggested adding UV light to the system to increase toxicity of the ozone, however, this was not tested. The extremely high ozone levels used and the long residence times in the system are unacceptable for real time disinfection of pathogen-contaminated air.

The present neutralization system (hereinafter "the neutralization system") can neutralize airborne pathogens in large volumes of moving, contaminated air in real time; such a method and apparatus has never been reported before. The amount of ozone released from the present neutralization system into an HVAC system can be minimized to comply with environmentally acceptable amounts of ozone. Further, the present system depends on a reagentless chemical process and therefore can be a stand-alone system. A HEPA filter placed upstream from the neutralization system would remove approximately 99.97% of the airborne particulates before contaminated air entered the neutralization system. HEPA filters have an additional important use in that they remove spores that are known to be especially difficult to neutralize in circulating air. However, HEPA filters do not capture viruses. Activated carbon filters also remove particulate matter and are useful when disposed either upstream or downstream from the pathogen neutralization system. placed, between pre-existing high efficiency particulate air (HEPA) filters and activated carbon filters.

Advantages of the UV/ozone pathogen neutralization system include the following:

- The neutralization system can be installed in conjunction with other air pathogen neutralization technologies such as installing this neutralization system after air has been passed through a pre-existing HEPA filter system.
- The neutralization system is activated and operated electrically.
- The major components of this neutralization system are commercially available.
- The neutralization system is reagent-less and requires no replaceable chemicals. The ozone is generated from building air as the source of oxygen. Water can be provided from the buildings' low-pressure supply.
- Stable by-products of the process are oxygen and water. The highly reactive, free radical intermediates are short-lived and low amounts of ozone exit the neutralization system.
- The neutralization system requires a minimum of maintenance.
- The pulsed UV light can be operated in tandem or independently with the ozone generator used to provide ozone to the neutralization system.
- Commercially available humidity, particle sampling, ozone, and UV light sensors allow the neutralization system to be microprocessor controlled and continually balanced.
- Other embodiments include an open-pore metal foam support in the neutralization system that produces a beneficial low-pressure drop across the neutralization system and it provides the medium in which concentrations of ozone and its highly active radical intermediates diffuse and react with airborne pathogens.
- Three pathogen neutralization approaches are combined by the present invention: ozone sterilization, UV sterilization and sterilization by the free-radical ozone intermediates.
- The neutralization system can be built to be self contained with an ozone generator and a portable re-circulating water reservoir that permits water to be reused), and it can be made in different sizes so that it can be adapted for installation in cars, tanks, aircraft, etc.

Figure 1:
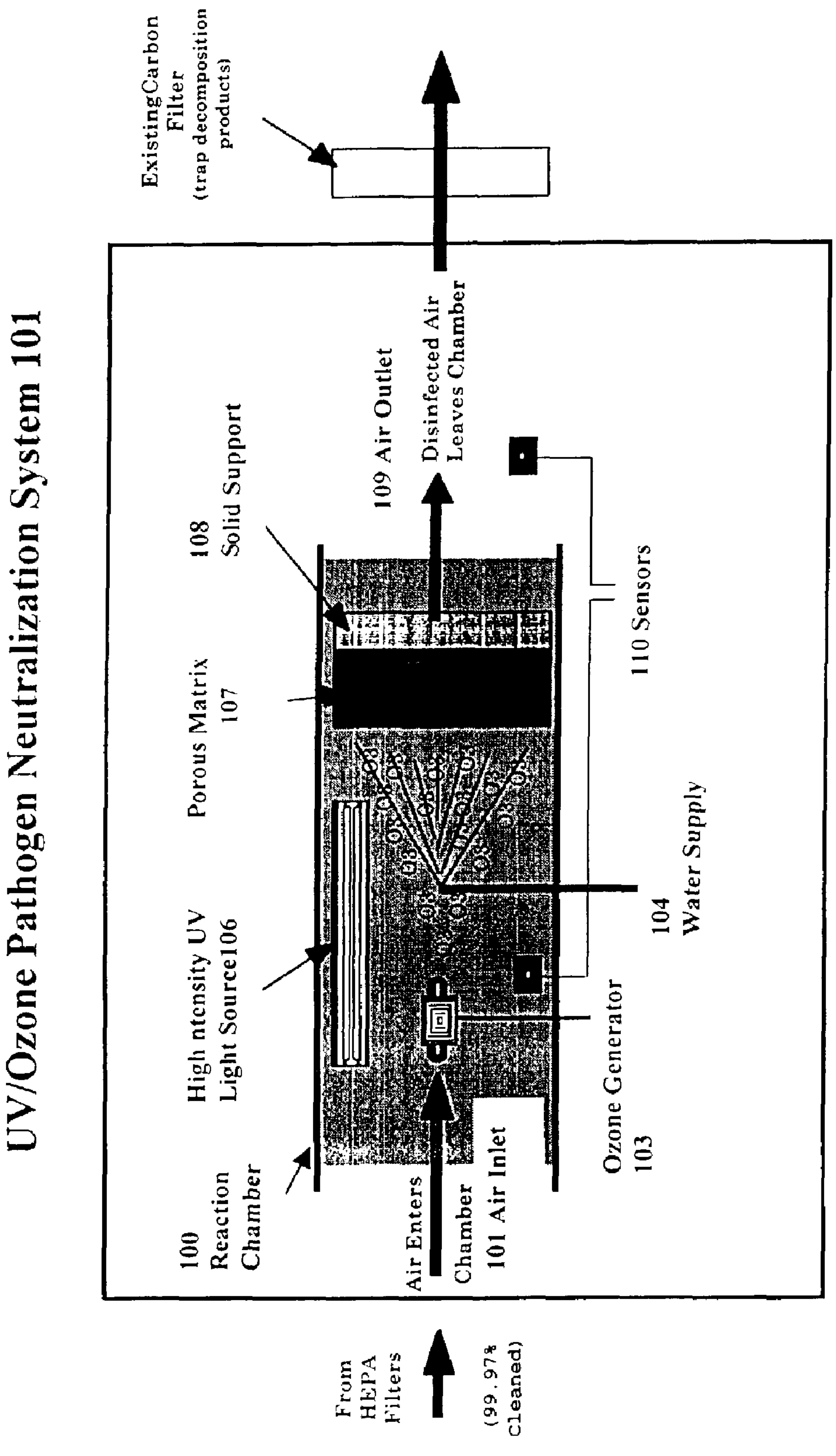
FIG. 1 is a block diagram of an embodiment of the UV/ozone pathogen neutralization system having the ozone generator 103 disposed inside the flow-through reaction chamber 100.

All embodiments of the neutralization system have a flow-through reaction chamber 101 that has a chamber air inlet 102 to admit pathogen-contaminated air, and a chamber air outlet 109 to release pathogen-neutralized air. A space is defined between the chamber air inlet and outlet that accommodates the passage of moving air through the reaction chamber. The reaction chamber always contains one or more UV light sources 106 that emit high intensity, broad-spectrum UV light. In the embodiment shown in FIG. 1, the reaction chamber also contains an ozone generator 103 that releases ozone gas to the interior of the reaction chamber, and a water supply line 104 with a nozzle 105 at the end for spraying fine mist or introducing water vapor or humid air into the reaction chamber. In some embodiments, the reaction chamber is lined with an UV reflective coating or is built of an UV reflective material. In some embodiments an optional porous matrix 107, such as metal foam, is installed in the reaction chamber to provide additional surface area on which the ozone gas and ozone free radicals can react with the pathogens. In one embodiment, the porous matrix covers the reaction chamber air outlet 109 to assure that all air leaving the neutralization system passes through the metal foam matrix. The porous matrix is recommended where large volumes of air are being decontaminated. The neutralization may further contain an optional solid support coated with one or more ozone removal catalysts 108. The neutralization system may have sensors to monitor ozone, humidity, temperature, and/or ultraviolet light levels. In one embodiment the neutralization system is fully automated.

In some embodiments, the reaction chamber is designed to have more than one chamber air inlet and outlet; this permits the installation of the neutralization system at locations where several ducts converge. Similarly, the reaction chamber may have more than one chamber air outlet. In other embodiments the neutralization system is entirely self-contained. In the entirely self-contained systems, the ozone generator and a water reservoir are placed inside the reaction chamber. The water reservoir is connected to the water supply line. Thus, the neutralization system can be scaled down to a size that is portable, and suitable for use in vehicles such as military tanks.

Another embodiment of the neutralization system is illustrated in FIG. 2, in which water and ozone are mixed together in a mixing chamber 212. The ozone/water mixture is then introduced into the reaction chamber through a spray nozzle 105. Premixed water and ozone gas mixture is sprayed into the reaction chamber through nozzle 205. Water is supplied from water reservoir 204 connected to the water/ozone supply line 212. An ozone generator 203 is connected via an ozone conduit 203*a* to the water/ozone supply line 212 at conduit opening 212*a*. The ozone generator, water reservoir and water/ozone-mixing chamber can be disposed either outside or inside the chamber.

An optional porous matrix 207 made of metal foam that provides additional surface area on which the ozone gas and ozone free radicals can react with the pathogens, is included in the neutralization system of FIG. 2. In the embodiment illustrated in FIG. 2, the neutralization system further contains an optional solid support coated with one or more ozone removal catalysts 208. In some embodiments the solid support 208 is immediately adjacent to or placed near the chamber air outlet 209, and after the porous matrix 207. The addition of a solid support to the neutralization system enables the safe use of relatively high amounts of ozone. The level of ozone in outgoing air leaving the neutralization system can be monitored with sensors to prevent hazardous levels of ozone from being released.

The neutralization system can be operated at a wide range of ambient temperatures, including in air cooled by air conditioning or heated in the winter, desert air that is dry and hot, or very cold air. In some embodiments, the chamber is heated by the installation of heating coils that can be located on the outside of the chamber, or in the chamber walls. Similarly, the reaction chamber can be cooled using any known technology; such as with a cooling tower or cooling coils that remove heat from the neutralization system.

Introduction of Ozone and Water Vapor into the Flow-Through Reaction Chamber Any ozone generator can be used in the present inventions including a corona discharge generator. While ozone can be produced using UV light, this method is presently inefficient, unreliable and very costly to service. However, should the technology advance for generating ozone using UV or other methods, it can be incorporated into the present neutralization system. Electric corona discharge generators produce large quantities of ozone rapidly. The passage of a high voltage, alternating electric discharge through an environmental air stream containing oxygen breaks down molecular oxygen to atomic oxygen. Some of the atoms of oxygen thus liberated reform into ozone, while others simply recombine to again form oxygen. In order to control the electrical discharge and maintain a “corona” or silent discharge and still avoid arcing, a dielectric space or discharge gap is formed, using a dielectric material such as glass or ceramic. Typically, an electric ozone generator is powered from a 240 volt, 50 Hz, AC power supply. Commercial ozone generators are available in various sizes and shapes with various capacities for generating ozone.

Ozone generally occurs in natural settings at around 0.02 ppm (parts per million), but it can be found as concentrated as 0.10 ppm, at which level it keeps pathogens in check without being harmful to animals or man. Prolonged exposure to much higher levels of ozone may lead to discomfort, headache, and coughing, warning humans to leave the space and seek better air. OSHA has stipulated that the safe allowable level of residual ozone is 0.1 ppm for continuous exposure throughout an entire 8-hour day for 5 days a week. As soon as ozone is formed in the generator and introduced into the reaction chamber, it either begins to decay back into stable oxygen, or it reacts with water in the presence of high intensity, broad spectrum UV light to form highly active, short-lived intermediates. The maximum half-life of ozone is approximately 30 minutes. However, in practice the half-life is usually much shorter due to interactions with contaminants in the air and contact with surfaces such as walls and carpets. Exposure to ozone levels four to five times the approved levels for short periods of time have no adverse effects because the ozone itself decays back to oxygen rapidly. The present neutralization system can be operated in continuous or intermittent modes. The high intensity UV light source and the ozone generator are typically operated in tandem, but can be operated independently.

Broad Spectrum UV Light Source is Installed in the Chamber

Broad spectrum UV light is used in the present neutralization system primarily to cause ozone to react with water (vapor or droplets) to form highly active free radical intermediates that in turn react with and destroy pathogens. However, UV radiation is intrinsically toxic to some pathogens, causing radiation damage to the pathogen’s DNA so that it cannot reproduce. High levels of UV radiation are considered lethal for most microorganisms, including bacteria, fungal spores, viruses, protozoa, nematode eggs and algae. That part of the UV light spectrum known to kill or neutralize most pathogens is between 100-400 nanometers, which just below visible light. However, UV neutralization system is more effective when irradiating surfaces than on airborne pathogens.

Pathogenic bacteria are the easiest pathogens to neutralize; viruses and spores are more resistant. Spores of the *Bacillus* species possess a thick protein coat that consists of an electron-dense outer coat layer and a lamella-like inner coat layer. This coating reduces the effect of UV irradiation on the pathogen’s DNA.

Suitable for use in the present pathogen neutralization system are incandescent, quartz or mercury vapor lamps. UV light can be continuous or pulsed, and high intensity UV lights are preferred. In a flashing UV light, each high power flash or pulse lasts only a few hundred millionths of a second. Typically flashes of UV light last from about 1 to about one millionth of a second in duration, and have a frequency of from about 1 to 10 flashes per second. The flashes of UV light are in the range of from about 100-400 nm, typically 250-350 nm. The duration, wavelength, and intensity of the UV light can be adjusted to optimize the effect on various pathogens. Flash frequency can vary from 1-1000 per second as determined by experimentation.

Addition of a Porous Matrix to the Chamber Increases Sterilization Rate and Amount of Sterilization A porous matrix placed inside the reaction chamber provides an increased surface area on which the ozone intermediate breakdown products contact and react with airborne pathogens in a micro-solvent environment. The solvent is the water that condenses on the pathogens. In the examples, the porous matrix used was a DUCOCEL® aluminum metal foam having a pore size of 40 PPI (pores per square inch) and 8% density. The DUCOCEL®matrix adds a large surface area on which the ozone intermediates and pathogens can interact without causing a very low-pressure drop that did not noticeably impede the airflow. In some embodiments, the porous matrix is removable and reusable. The volume, thickness and density of the porous matrix can be varied depending on the volume of contaminated air being passed through the neutralization system and the size of the chamber air outlet.

Any solid porous matrix can be used that increases surface area without blocking air outflow from the neutralization system or inhibiting the formation of the highly reactive ozone intermediates. In some embodiments, metal foams that have antibacterial activity are used, such as copper and silver. Porous matrices of plastics, polymers, particle balls, threads and/or ceramics can also be used.

In some embodiments, the porous matrix is coated with one or more non-volatile antibacterial, antiviral and antispore agents that increase pathogen neutralization without inhibiting the formation of the highly reactive ozone intermediates. This is particularly advantageous where a pathogen is highly resistant to neutralization. Routine experimentation will determine which additives are the most effective, and this will vary depending on the pathogen. Where very large volumes of air are moved through the UV/ozone neutralization system, one or more fans may be installed as was done in the examples.

The UV/Ozone Pathogen Neutralization System Neutralizes Airborne Bacteria, Spores and Viruses.

The Examples show that the neutralization system is effective in neutralizing on all of the airborne pathogens tested: active, vegetative airborne bacteria (*Erwinia herbicola*-Example 2), viruses (Bacteriophage MS2 Virus), and (*Bacillus globigii* spores Example 3). In examples 2 (bacteria) and 3 (spores), the New Brunswick Scientific Microbiological Air Sampler Series STA-204 (a slit sampler) was used to collect samples of incoming air just before it entered the neutralization system, and of outgoing air just after leaving the system. The slit sampler works by drawing a known total volume of air through a slit opening by vacuum. A pressure drop that occurs across the slit causes the air with its entrained contaminants to accelerate to a higher velocity. The airborne pathogen contaminants, because of their heavier mass, are impacted onto the surface of a sterile petri dish placed on a rotating, timed turntable. Only the small area of surface of the agar that is located just below the slit is exposed to the contaminated air. Thus as the dish rotates, different sectors of agar are exposed. A sample time was selected of thirty minutes for *Erwinia herbicola* and *Bacillus globigii* experiments, and a sample time to ten minutes was selected for the bacteriophage MS2 experiments (Virus). The sampler is set so that the duration of the experiment is equivalent to one complete revolution of the petri plate. When the sample time has elapsed, no further air sample is taken. A particle distribution guide can be used to estimate the time at which contamination occurred. The guide is a Mylar disk that is divided into thirty segments by lines that emanate from near the center to a marker circle near the outer edge. The bottom of the petri dish is marked with a line to indicate the position of the dish at time zero. This makes it easy to line up the particle guide.

In the examples, samples of incoming air taken continuously were impacted onto the System air inlet plate, and samples of outgoing air were impacted onto the System air outlet plat for each experiment. In a first experiment ordinary room air that was passed through the system with the water, ozone and UV light off, did not exhibit any pathogen contamination (FIGS. 5A-B and 6A-B). This showed that the neutralization system was clean and that the room air had undetectable levels of pathogens. The circles in the photographs are air bubbles, not pathogen colony forming units (CFU).

Figures 5A, 5B:
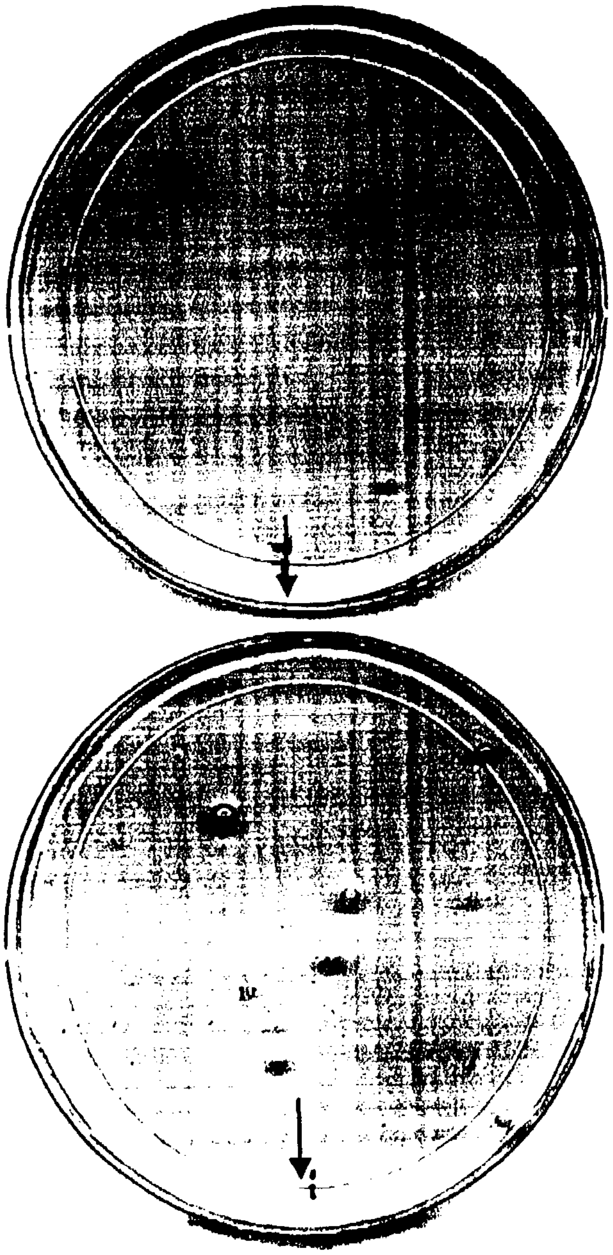
FIG. 5. A-H are photographs of plates that were exposed to air going into and out of the flow-through reaction chamber in experiments designed to test the ability of the neutralization system to neutralize a large excess of airborne, vegetative *Erwinia herbicola* bacteria. The thirty minute recording starts at arrows and rotates counterclockwise.
Figure 5D:
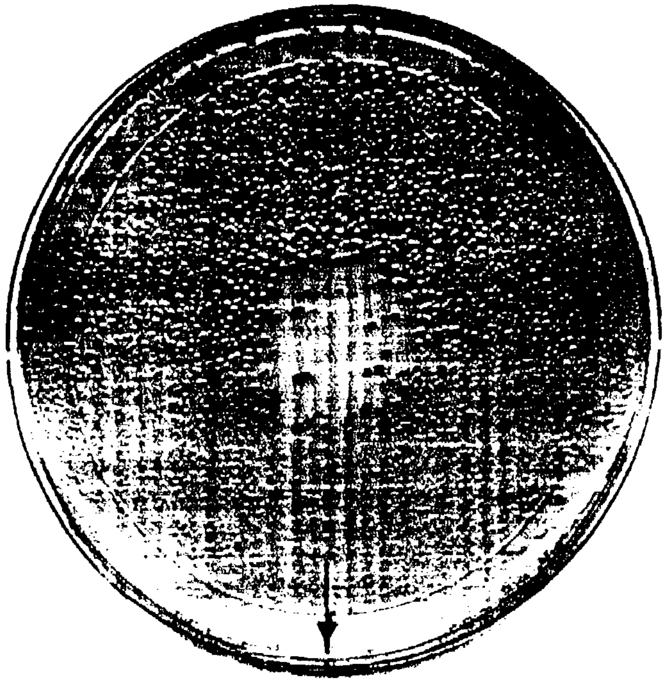
Figure 5C:
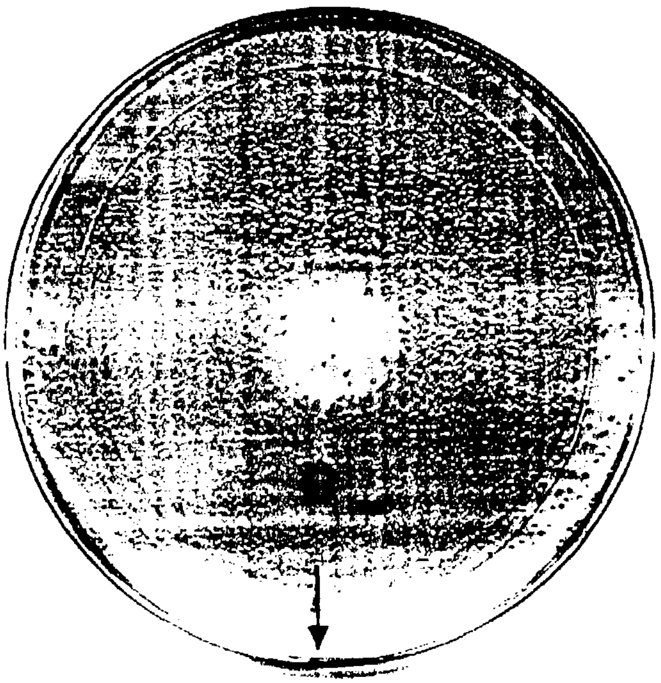
Figure 5E:
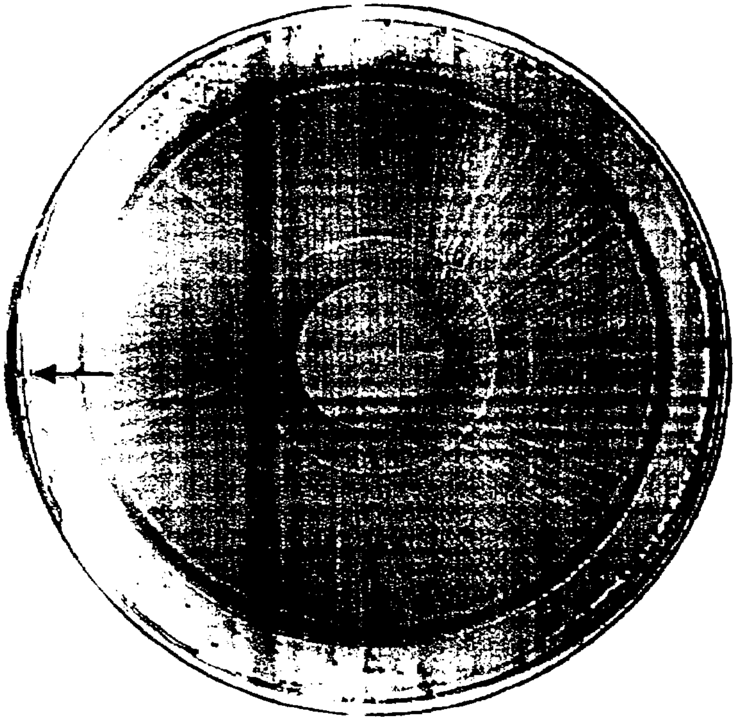
Figure 5F:
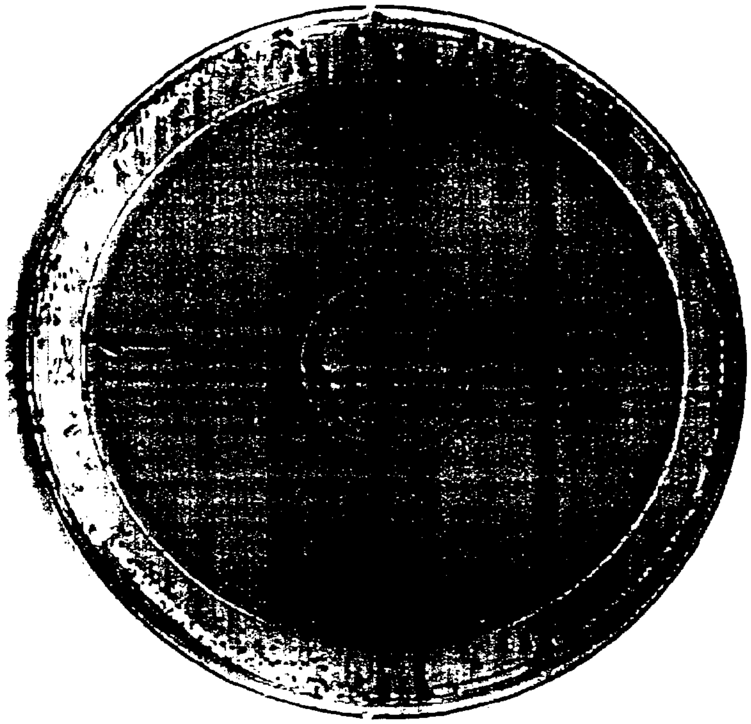
Figure 5G:
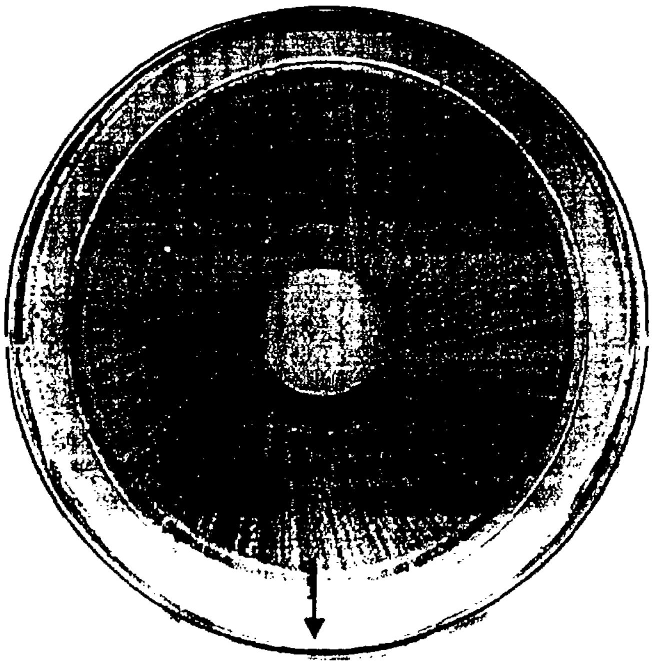
Figure 5H:
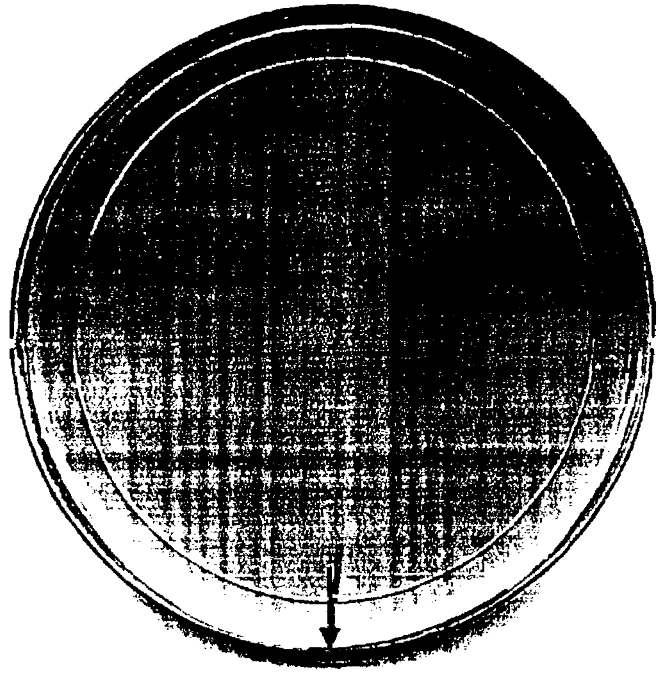

In Example 2, excessive amounts of *Erwinia herbicola* bacteria were introduced into the chamber with all systems off (water off, ozone generator off, and UV off). As expected, both the System Inlet and System Outlet plates were overgrown with bacteria, with CFU too numerous to count (FIGS. 5*c* and 5*d*). This showed that the nebulizer introduced a large excess of bacteria into the reaction chamber, and that the outgoing air remained contaminated. In another experiment, airborne bacteria were introduced into the chamber air inlet with the only the water (Water on, Ozone Off, UV Off). This experiment resulted in both the System Inlet and Outlet plates being overgrown with bacteria, such that the CFU were too numerous to count. FIGS. 5E and F. In the last experiment, the neutralization system was fully operative (Water on, Ozone On, UV On). In this case, the System Inlet plate was predictably overgrown with bacteria, such that the CFU were too numerous to count. However, the System Outlet plate had no CFU at all. This result shows that all of the bacteria that had been deliberately introduced to and passed through the neutralization system in real time were neutralized, so that nothing grew on the System air outlet plate even under ideal conditions in an incubator. FIGS. 5*g* and 5*h*. This showed that the neutralization system was effective in neutralizing or killing all of the active, vegetative airborne bacteria (*Erwinia herbicola*-Example 2).

Figure 6A:
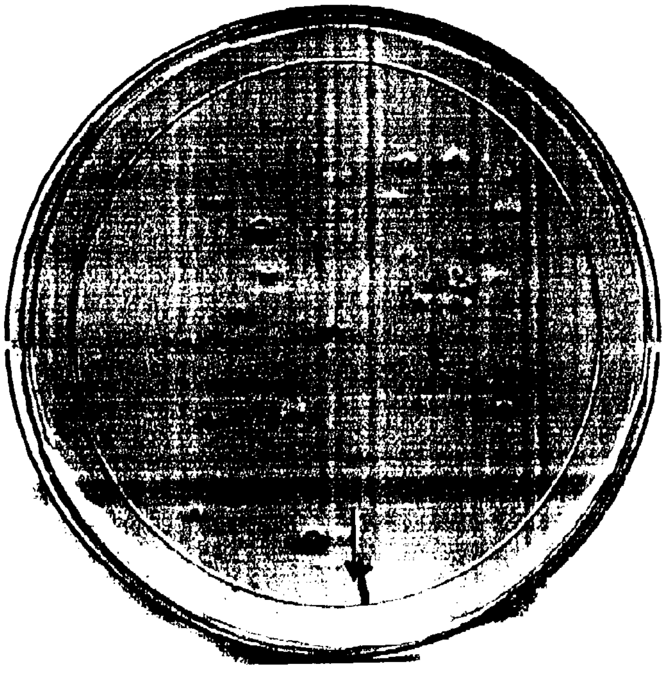
FIG. 6. A-H are photographs of agar plates that were exposed to air going into and out of the flow-through reaction chamber in experiments designed to test the ability of the neutralization system to neutralize a large excess of airborne *Bacillus globigii* spores. The thirty minute recording starts at arrows and rotates counterclockwise.
Figure 6B:
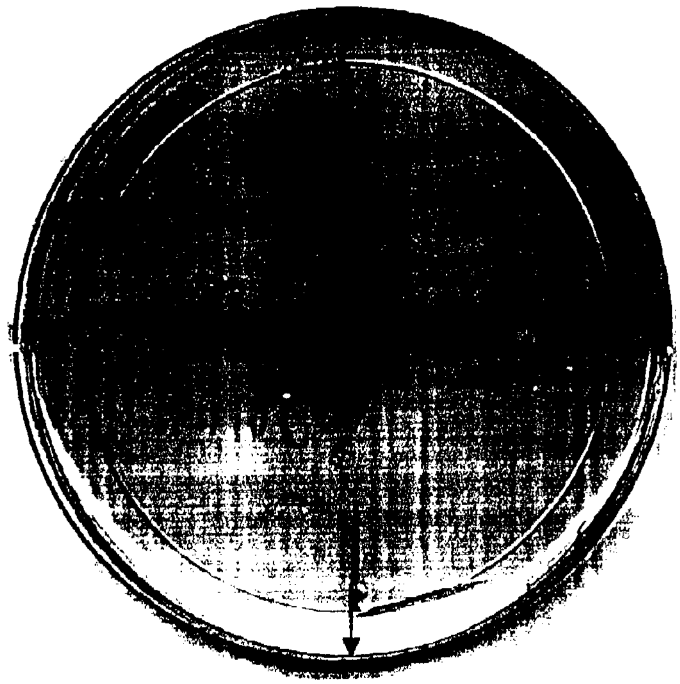
Figure 6C:
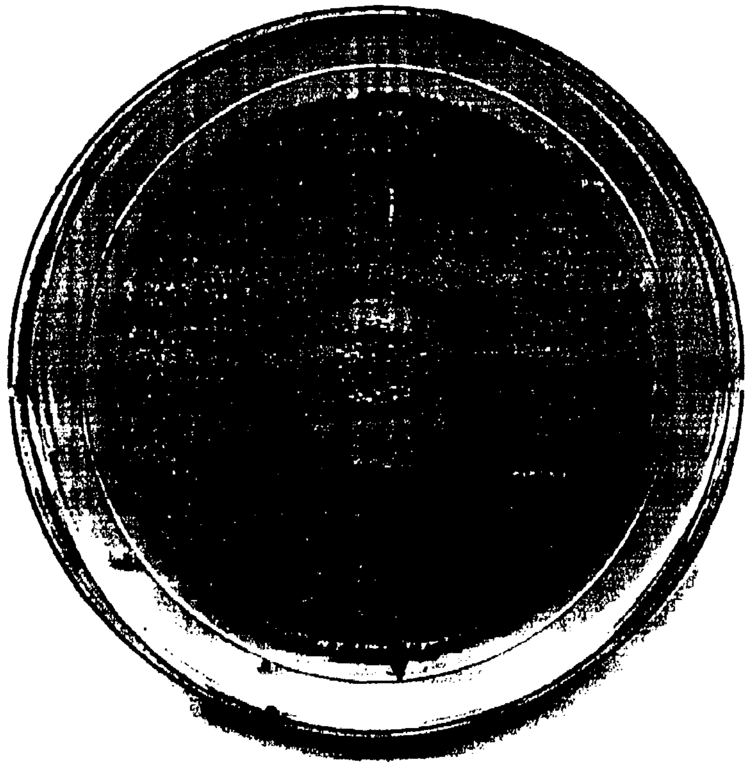
Figure 6D:
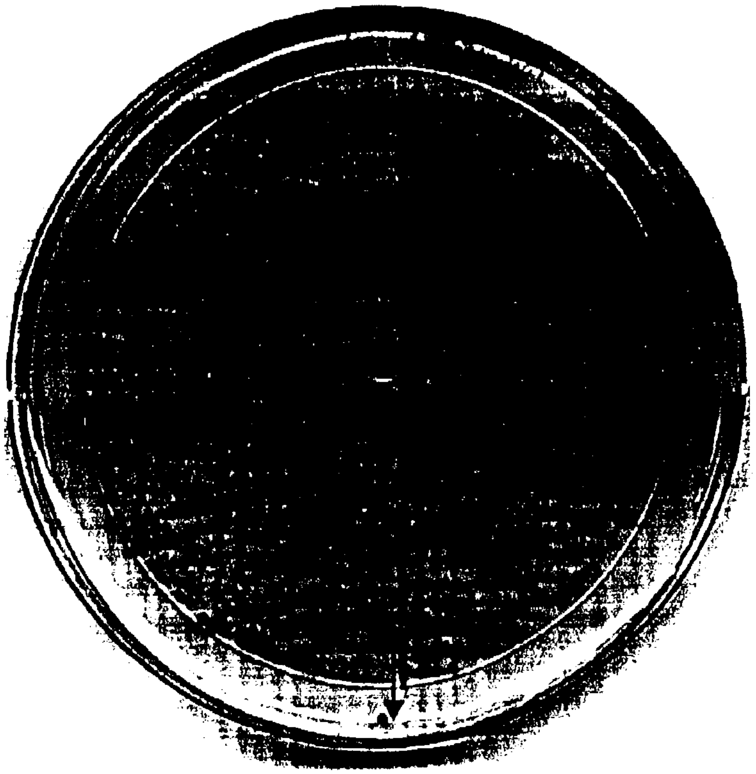

Example 3 tested the ability of the system to neutralize airborne *Bacillus globigii* spores. Spores are much more difficult to kill than are vegetative bacteria. As was expected, both the System inlet and System outlet petri plates were overgrown with bacteria when spore-contaminated air was passed through the inoperative neutralization system with all systems off (water, ozone and UV off, fan only). (FIGS. 6C and 6D). In a third experiment, airborne *Bacillus globigii* spores were introduced into the incoming air with only the fan and water on (ozone, UV off). Again, both the System inlet and System outlet petri plates were overgrown with bacteria.

In a third experiment, airborne *Bacillus globigii* spores were introduced into the incoming air with the full neutralization system on (ozone generator on, ultraviolet light on, and water mist on). The System Inlet plate was predictably overgrown with bacteria (FIG. 6E), however, the System Outlet plate (FIG. 6F) showed about 1-2 orders of magnitude neutralization compared to the System Inlet. Only about 15 CFU per sector were counted on the System Outlet plate. While the neutralization system did not neutralize all incoming airborne spores of *Bacillus globigii*, the level of spores deliberately introduced to the reaction chamber was extremely high. Thus the spore neutralization levels obtained in real time represents a significant breakthrough in technology. Installing a HEPA filter in front of the chamber air inlet to filter the room air before it entered the reaction chamber, would trap a about 97% of the airborne pathogens before they enter the neutralization system. Thus, in areas of high risk, a HEPA filter should be used before incoming air enters the present neutralization system.

Bacteriophage MS2 Virus does not grow on agar, so an indirect assay was set up to assess the levels of the virus in incoming contaminated air and in outgoing disinfected air as is described in Example 4. To capture samples of the virus, incoming and outgoing air was bubbled through water and collected continuously during the ten-minute experiments using the AGI-30 sample tubes. Bacteriophage MS2 is aggressive toward *E. Coli*, causing lysis of the cells, hence killing them. To assess the amount of bacteriophage MS2 in incoming contaminated and outgoing pathogen-neutralized disinfected air, sterile plates were swabbed with samples collected from the AGI-30 tubes. The plates were then covered with the *E. coli* host organism and incubated. MS2 kills *E. Coli* bacteria. Plates were analyzed by looking for the presence of lytic plaques in otherwise confluent lawns of bacteria. Lytic plaques correlate with the presence of MS2 in the air sample. Lysis of *E. coli* had to be directly observed visually on the plates, as photographs did not enable accurate counting of lytic plaques. Both System Inlet and System Outlet plates grew confluent lawns of *E. Coli* with no signs of plaque formation from lytic activity when ordinary room air was passed through the neutralization system.

When high levels of Bacteriophage MS2 were passed through the system with the neutralization system off, both System Inlet and System Outlet plates had confluent lawns of *E. Coli* with readily apparent lytic activity in the form of distinct plaques throughout both plate sets. These results indicate that virus effectively passed through the system and was not lost due to adsorption or desiccation effects inside the test chamber. In a last experiment, Bacteriophage MS2 was passed through the system with the neutralization system on (water on, ozone generator on, UV light on). As expected, the system inlet plate had confluent lawns of *E. Coli* host organism, with lytic activity that was readily apparent in the form of clear plaques in the lawns. The plaques were hazy due to the growth of resistant *E. coli* host cells, but they were nonetheless distinct, indicating the presence of bacteriophage MS2 in the incoming air. But the System outlet plate had confluent lawns of the *E. Coli* host with no signs of lytic activity. This indicates that 100% of MS2 that was introduced into the test chamber was inactivated/neutralized.

The results show that the neutralization system of the present invention, which generates highly active free radicals from the reaction of ozone with water in the presence of high intensity, broad sepctrum UV light, is 100% effective in neutralizing MS2 bacteriophage and *Erwinia herbicola* bacteria. While less than completely effective neutralizing *Bacillus globigii* spores (a simulant for Anthrax), the present neutralization system was effective to at least about 1-2 orders of magnitude kill.

Solid Support Coated With Ozone Removal Catalysts Prevents Ozone Escape

A solid support coated with one or more ozone removal catalysts known in the art, can be installed in the reaction chamber to prevent ozone from building up in an enclosed space or building into which outgoing air is discharged. In one embodiment, the solid support is removable and can be changed when the catalysts have been used up. In another embodiment, the solid support itself is reusable and can be recharged with fresh ozone removal catalysts before being reintroduced into the pathogen neutralization system. Ozone removal catalysts that can be used in various embodiments include an all-aluminum catalyst, a carbon-supported metal oxide catalyst, copper chloride-coated carbon fibers, carbon-iron aerosol particles aluminum, and metal catalysts. *Ozone-destruction catalysts*, Rodberg et al. 1991. CARULITE® (an inorganic oxide) made by Carus Chemical Company is another ozone removal catalyst. Any solid support can be used, especially glass or silica which substances can catalyze ozone decomposition.

The unstable, highly active ozone free radical intermediates form stable final products including water vapor and oxygen that can be released back into the environment. The decay of ozone to stable oxygen is accelerated by surfaces that act as substrates for the decay process. Some of the ozone in the chamber is also converted by the broad-spectrum UV to highly reactive, short-lived free radicals that decay very quickly.

To optimize pathogen neutralization, the pH of the water introduced into the system can be adjusted. Routine experimentation will determine the optimum pH for neutralizing various pathogens. Where neutralization of a given pathogen is enhanced by acidic pH, the water can be treated with acetic acid to obtain the desired pH before it is sprayed into the neutralization system. Alternatively, a basic pH can be obtained where beneficial.

The present invention also provides a method of neutralizing airborne pathogens in air circulating through air conditioning or heating systems having one or more ducts that move and direct the circulating air. The neutralization systems described above can be installed in existing heating and air conditioning ducts. This can be accomplished by removing a section of the existing duct to accommodate the neutralization system reaction chamber, and connecting the reaction chamber to the existing duct at the chamber air inlet and outlet. The pathogen neutralization system is installed so that pathogen contaminated air passes into the chamber from the existing duct through the air inlet, and pathogen-neutralized air leaves the neutralization system through the air outlet from which it passes back into the existing duct for recirculation. To assure that all contaminated air enters and passes through the neutralization system, the chamber air inlet and outlet are adapted to fit the existing ducts using methods known in the art so that no air is allowed to bypass the system. In one embodiment, the chamber air inlet/outlet is adapted to fit an existing building air duct using a flange, with a rubber O-ring between the chamber wall and the flange to prevent air leaks.

Although the steps of the method for neutralizing pathogens using the neutralization system of the present invention are described in a particular order below, in other embodiments the steps may occur in a different order or overlapping in time. The method of neutralizing airborne pathogens in ventilated air involves the steps of:

a. directing circulating air contaminated with pathogens into a flow-through reaction chamber;
b. introducing water vapor or water droplets into the reaction chamber;
c. introducing ozone into the reaction chamber;
d. irradiating the pathogen-contaminated air, water vapor or water droplets, and ozone with ultraviolet light to neutralize the pathogens in the contaminated air thereby creating pathogen-neutralized air, and
e. after the irradiating step, passing the pathogen-neutralized air out of the reaction chamber.

The method can be modified so that the step of introducing water vapor (which includes humid air), or small water droplets and the step of introducing ozone are performed by forming a mixture of water vapor, water droplets and ozone before introducing the mixture into the reaction chamber.

The method installing a pathogen neutralization system in ventilated air includes the steps of a. cutting an opening in an existing air duct in a structure and removing a section of it to accommodate the installation of the UV/ozone neutralization system;
b. installing the neutralization system in the existing duct by connecting the chamber air inlet and chamber air outlet of the system in sealing relation to the existing duct so that pathogen-contaminated air is blown into the reaction chamber through the chamber air inlet, and pathogen-free disinfected air leaves the system through the chamber air outlet;
c. turning on the neutralization system so that ozone, water and ultraviolet light are supplied to the reaction chamber as described herein;
d. passing contaminated air from the existing duct into the reaction chamber through the chamber air outlet,
e. permitting the highly active ozone free radical intermediates, ozone gas and ultraviolet light to react with the dispersed airborne pathogens in the contaminated air inside the reaction chamber thus neutralizing the pathogens, and
f. permitting the pathogen-free disinfected air to leave the reaction chamber through the chamber air outlet.

In some situations it may be desirable to install a HEPA filter either upstream from the chamber air inlet to remove 99.97% of all airborne particulate matter prior to air entering the neutralization system. The installation of the HEPA filter can increase the efficiency of the neutralization system. While effective at removing some airborne bacteria, HEPA filters do not remove viruses and spores. Activated carbon filters can also be used to remove airborne particulate matter.

Use of Surfactants, pH, Ultrasound, Microwaves to Increase Pathogen Neutralization To increase the effectiveness of ozone on airborne pathogens, especially spores, nontoxic surfactants (soap molecules) can be pre-mixed with the water and sprayed into the reaction chamber in some embodiments. It is thought that the surfactants increase the contact time between ozone and ozone free radicals and pathogens, thus facilitating pathogen neutralization. One or more nontoxic surfactants known in the art can be used.

Any means of disrupting or fracturing the coating protecting spores and other pathogens will increase pathogen neutralization in the present UV/ozone neutralization system by permitting the highly active free-radical ozone intermediates, free ozone and UV light to interact with the pathogen. Microwaves and/or ultrasound may help to break down the spore coating to make the spores more susceptible to ozone. Plasma DC glow discharge has been shown to be an effective sterilization method for medical devices on its own. The principle sterilization using plasma DC glow discharge is intense UV radiation in the 160-240 nm range. Therefore in other embodiments, the UV/ozone neutralization system further includes a plasma DC glow discharge UV tube, a microwave generator, and/or an ultrasound generator. As an alternative, contaminated air to be disinfected in the pathogen neutralization system can be treated before it is provided to the system by placing a means for producing microwave irradiation, plasma DC glow discharge, and/or ultrasound upstream near the chamber air inlet.

In yet another embodiment of the present invention, ozone, water and contaminated air are mixed together in a vortex mixer before being sprayed into the reaction chamber. All three components can be introduced through separate lines into the mixer, or water and ozone can be premixed before being introduced into the vortex mixer where they are further mixed with incoming contaminated air mixture.

The UV/Ozone Pathogen Neutralization System Completely Neutralized Airborne *Erwinia herbicola* Bacteria and the Bacterial Virus MS2 (A Simulant for Viruses Such as Smallpox) in Real Time The examples below show that complete pathogen neutralization was obtained when air contaminated either with high levels of vegetative cells of the bacteria *Erwinia herbicola* or the bacterial virus MS2, (a simulant for viruses such as smallpox-Example 4) was directed to and passed through the fully activated neutralization system in real time. The neutralization system shown in FIG. 2 was used for all experiments, with the exception that the solid support with the ozone removal catalyst 208 was not included.

Spores are the most difficult pathogen to neutralize due in part to the thick protective outer coat. The results in Example 3 show that when very high levels of *Bacillus globigii* (13G) spores (a simulant for Anthrax) were passed through the fully activated neutralization system in real time, about 1-2 magnitude neutralization rate was obtained in initial testing. This rate can be optimized by adjusting the ozone level, amount of water, and thickness of the metal porous matrix using routine experimentation.

The present neutralization method is based on an unexpected synergy that occurs when ozone is irradiated with intense broad-spectrum UV light in the presence of water vapor or droplets. The neutralization system and related method of neutralizing airborne pathogens thus provides a three-way method of attacking and neutralizing pathogens, 1- with ozone, 2- with ultraviolet light and 3- with the highly reactive, short-lived ozone free radical intermediates. It has been discovered that the neutralization system of the present invention provides a highly effective means of neutralizing a wide spectrum of airborne pathogens including bacteria, viruses and spores.

In the foregoing specification, the invention has been described with reference to specific embodiments thereof. It will, however, be evident that various modifications and changes may be made to the inventions without departing from the broader spirit and scope of the invention. The present application will be described in further detail, while referring to the following non-limiting examples.

EXAMPLES

Example 1

A. The Neutralization System

The neutralization system used in this experiment is shown in FIG. 2, with the exception that the solid support 208 with ozone removal catalysts was not included, and the system also included a fan to help pull air through the system. The fan was turned on in all experiments. A CD-5 GENESIS™ corona discharge ozone generator made by Del Industries, Inc. with maximum output of 5 g/hr was disposed outside the reaction chamber as shown in FIG. 2. Downstream from the ozone generator 203 and ozone conduit 203*a*, is a water reservoir 204 that releases a stream of water into the water/ozone conduit 212. As the water stream flows through the water/ozone conduit, it creates a vacuum that helps to pull the ozone gas exiting the ozone generator 203 through ozone conduit 203*a* into the water/ozone conduit 212 at conduit opening 212*a*. The UV light source (206 consisted of two BioAire —UV Lights Model BUV 24DE Double Ended Fixtures. The brand of light is not critical; however, more powerful UV lights are preferred. New pulsed UV light sources that are extremely powerful are available and may be used in the present invention. The size of the reaction chamber was 45 inches length×21 inches height×23 inches diameter. The air inlet 202 and air outlet 209 were sized to fit tightly onto a commercially available flexible duct, to which duct they were connected with a flange or collar and a rubber seal. This tight connection prevents air loss and assures that all air leaving the air duct had passed through the UV/ozone neutralization system.

A porous metal foam 207 matrix was made of DUCOCEL® aluminum metal foam having a density of 8% and 40 PPI was used. Several sheets of the foam were cut and stacked until the stack measured 3.5 inches long and two inches in height and thickness. The matrix was held in place by restriction plates and was installed so that it was just in front of and covered the chamber air outlet 209 so that all air entering the system passed through the matrix before exiting the neutralization system.

Room air entered the neutralization system through the chamber air inlet. The humidity of the disinfected air leaving the reaction chamber varied from about 55 to 65 percent, and the temperature was room temperature. The ozone generator and the UV light source were operated in tandem throughout the experiments, and the neutralization system was operated in a continuous mode with the fan on during the experiments.

B. Introduction of Airborne Pathogens Into the Neutralization System.

In each experiment in Examples 2-4, microorganisms were introduced into the reaction chamber using the MICRO MIST™ nebulizer. *Erwinia herbicola, Bacillus globigii* spores and Bacteriophage M2 were all cultured in the laboratory using standard techniques well known in the art, until they attained a cell density of about 5.3×10(9) CFU/ml.

C. Collection of Samples of Incoming and Outgoing Air

For Examples 2 (bacteria) and 3 (spores), the New Brunswick Scientific Microbiological Air Sampler Series STA-204 (a slit sampler) was used to collect samples of incoming air just before it entered the neutralization system, and of outgoing air just after leaving the system. The slit sampler works by drawing a known total volume of air through a slit opening by vacuum. A pressure drop that occurs across the slit causes the air with its entrained contaminants to accelerate to a higher velocity. The airborne pathogen contaminants with their heavier mass, are impacted onto the surface of a sterile agar petri dish placed on a rotating, timed turntable. Only the small area of the surface of the agar that is located just below the slit is exposed to the air samples. As the dish rotates, different sectors of agar are exposed. The duration of the experiment (the sample time) was thirty minutes for *Erwinia herbicola* and *Bacillus globigii* experiments, and ten minutes for the bacteriophage MS2 experiments (Virus). The air sampler was set so that the duration of the experiment is equivalent to one complete revolution of the petri plate. When the sample time has elapsed at the end of the experiment, no further air sample is pulled through the sampler. A particle distribution guide can be used to estimate the time at which contamination occurred. The guide is a Mylar disk that is divided into thirty segments by lines that emanate from near the center to a marker circle near the outer edge. The bottom of the agar petri dish onto which the circulating air (either contaminated air or room air) is sampled, is marked with a line to indicate the position of the agar petri dish at time zero in order to accurately line up the particle guide.

When each 30-minute experiment was over, the agar dish was covered and taken to an incubator for 24 hours after which the plate was examined; colony-forming units (CFU) of bacteria were counted. In FIGS. 5 and 6, the arrow indicates the start of the recording at time zero; all plates rotated counterclockwise during the experiment. In all of the experiments, samples of both incoming and outgoing air were taken continuously throughout.

Example 2

The UV/Ozone Pathogen Neutralization System Completely Eliminated Large Amounts of Airborne Vegetative Cells of Erwinia The neutralization system was set up as described in Example 1. Various experiments were designed to assess the ability of the system to neutralize airborne *Erwinia herbicola* bacteria. In all experiments, air was passed through the system for thirty minutes while the system fan was continuously on. In certain of these experiments, large amounts of airborne vegetative cells of *Erwinia herbicola* bacteria (about $5.3\times10^{9}$ CFU/ml) were introduced into the air entering the reaction chamber through the air inlet as is described in Example 1B using a MICRO MIST™ nebulizer. Incoming air (with or without *Erwinia herbicola*) was sampled continuously just before entering the neutralization system via the air inlet, and outgoing air was sampled just as it leaves the system, as described in Example 1.

In FIGS. 5A-H, System inlet and System outlet plates (dishes) were continuously exposed to incoming and outgoing air respectively, and were analyzed for the presence of *Erwinia herbicola* during thirty-minute experiments. In a first experiment (FIG. 5A (inlet plate) and 5B (outlet plate)) room air was circulated through the reaction chamber with the neutralization system off (fan only) without introducing any pathogens. In FIGS. 5C and 5D, incoming air was intentionally infected with high concentrations of *Erwinia*, again with the neutralization system off (fan only). In FIG. 5E (inlet plate) and 5F (outlet plate) incoming air was infected intentionally with high concentrations of *Erwinia herbicola* while supplying water mist to the reaction chamber; the ozone generator and ultraviolet light of the neutralization system were off (water and fan only). In FIG. 5G (inlet plate) and 5H (outlet plate) incoming air was infected intentionally with high concentrations of *Erwinia herbicola* with the neutralization system fully operational: ozone generator on, ultraviolet light on, and water supply of the neutralization system on.

Control-No Bacteria, All systems Off-Fan Only

As a control, room air was drawn through the neutralization system (before any bacteria were intentionally introduced through the nebulizer) with all elements of the neutralization system off: water off, ozone generator off, and UV off. Both the System inlet plates exposed to incoming air and the System outlet plates exposed to outgoing air showed no CFU of bacteria after the thirty minute experiment. FIGS. 5A and 5B. The circles in the photographs are air bubbles, not CFU.

Test 1-Bacteria Were Introduced into the Chamber Air Inlet with All Systems Off-Fan Only When bacteria were introduced into the chamber air inlet with All Systems Off (water off, ozone generator off, and UV off), both the System Inlet and System Outlet plates were overgrown with bacteria, such that the CFU were too numerous to count. FIGS. 5C and 5D.

Test 2-Bacteria Were Introduced into the Chamber Air Inlet with the Water On, But the UV/ozone Systems Off When bacteria were introduced into the chamber air inlet with the Water on, but with the ozone generator and the UV light off, both the System Inlet and System Outlet plates were again overgrown with bacteria, such that the CFU were too numerous to count. FIGS. 5E and 5F.

Test 3-Bacteria Were Introduced into the Chamber Air Inlet with the UV/Ozone System Activated (Water On, Ozone On, UV On)

In a last experiment, bacteria were introduced into the chamber air inlet with the UV/ozone system fully activated (Water on, Ozone On, UV On). While the System Inlet plate was overgrown with bacteria, such that the CFU were too numerous to count, the System Outlet plate had no CFU at all. This shows that all of the bacteria that had been deliberately introduced into and passed through the neutralization system in real time were neutralized, and thus were unable to grow even under ideal conditions on a sterile agar plate in an incubator. FIGS. 5G and 5H.

Example 3

Large amounts of airborne vegetative cells of *Bacillus globigii* (13G) spores (a simulant for the anthrax spores), were introduced into the chamber air inlet of a neutralization system as described in Example 1 using a MICRO MIST™ nebulizer under several different sets of conditions. *Bacillus globigii* spores are known to be particularly difficult to neutralize. In all experiments, air was passed through the system for thirty minutes while the system fan was continuously on.

Control-No Spores, All Systems Off-Fan Only

As a control, room air was drawn through an inactive neutralization system before any spores were intentionally introduced. The water was off, the ozone generator was off, and the UV light was off. Both the System inlet plates exposed to incoming air and System outlet plates exposed to outgoing air that had passed through the inactivated neutralization system, showed no growth of bacteria after the thirty minutes that air was passed through the reaction chamber. FIGS. 6A and 6B. The circles in the photographs are air bubbles, not CFU.

Test 1

Spores were Introduced into the Reaction Air Inlet with All Systems Off-Fan Only When spores were introduced into the reaction chamber air inlet with All Systems Off (water off, ozone generator off, and UV off), both the System Inlet and System Outlet plates were overgrown with bacteria, such that the CFU were too numerous to count. FIGS. 6C and 6D. Some of the CFU in the System Outlet plate, FIG. 6D, showed clumping of colonies.

Test 2

Spores were Introduced into the Reaction Air Inlet with Water On and Fan On

Figure 6E:
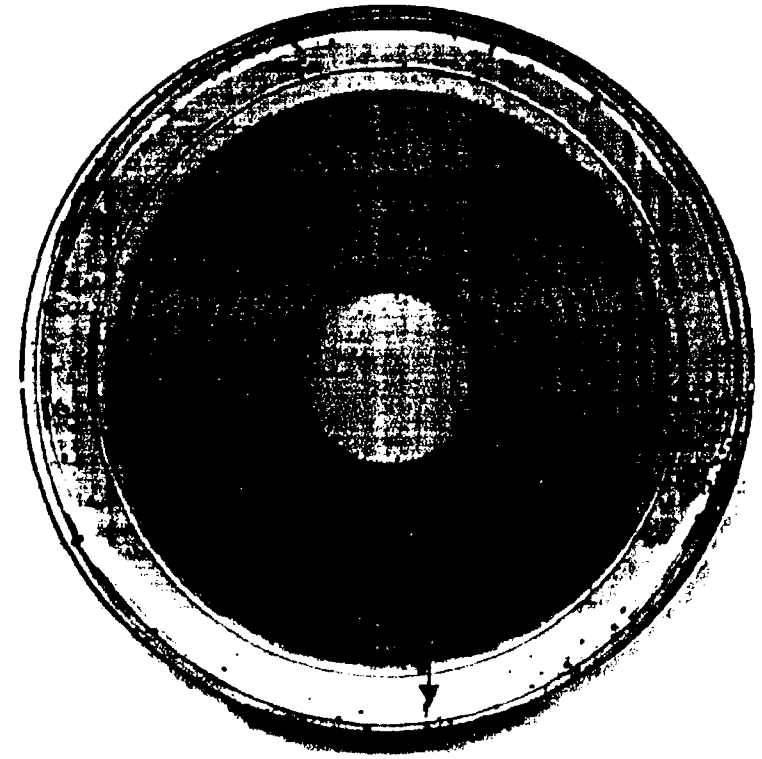
Figure 6F:
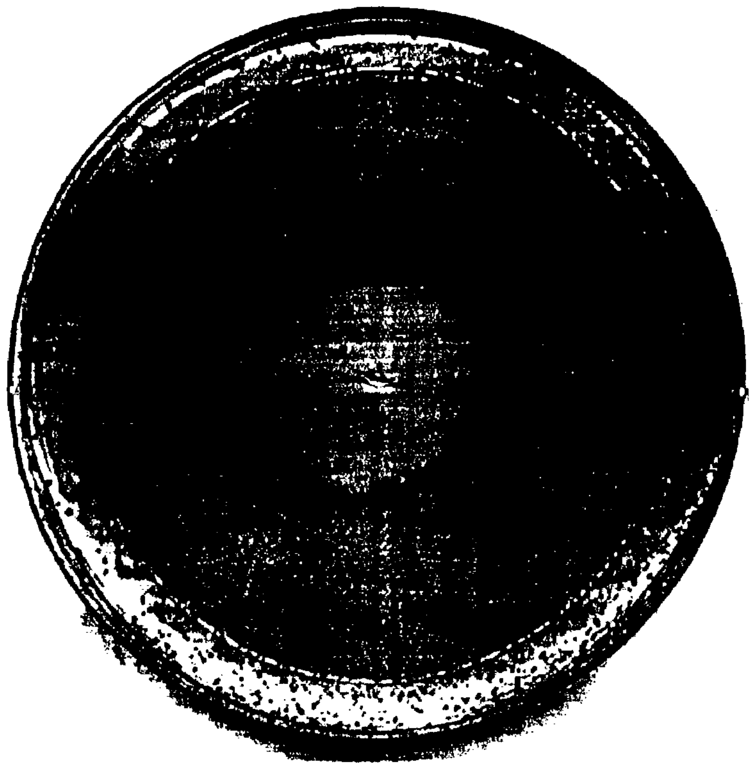
Figure 6G:
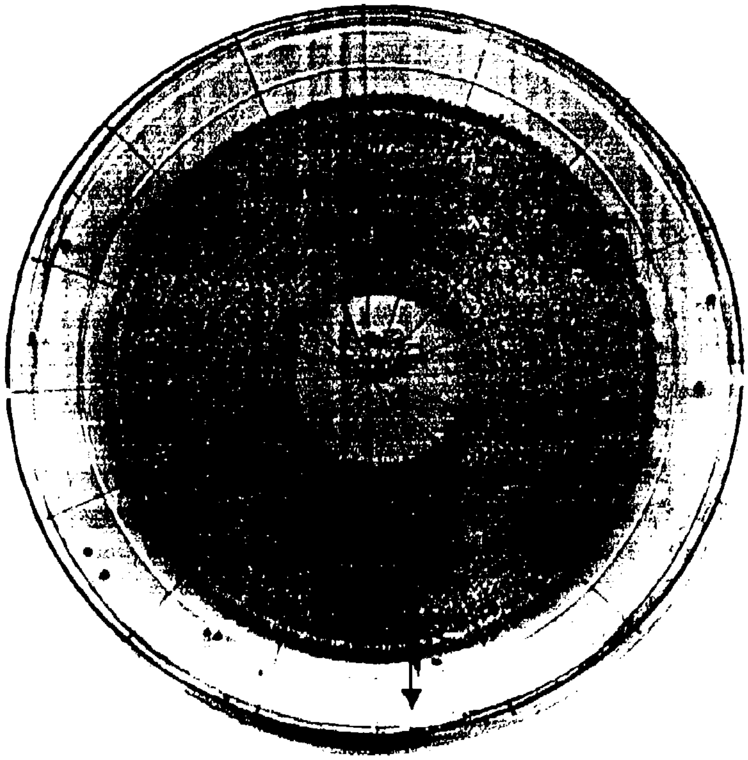

In FIG. 6E System Inlet and 6F System Outlet incoming air was infected intentionally with high concentrations of spores while supplying water mist to the reaction chamber; the ozone generator and ultraviolet light of the neutralization system were off (water and fan only). The results show that both inlet and outlet plates were overgrown with spores.

Test 3-Spores were Introduced into the Reaction Chamber Air Inlet with the Complete UV/Ozone System Activated (Water On Ozone On, UV On, Fan On)

Figure 6H:
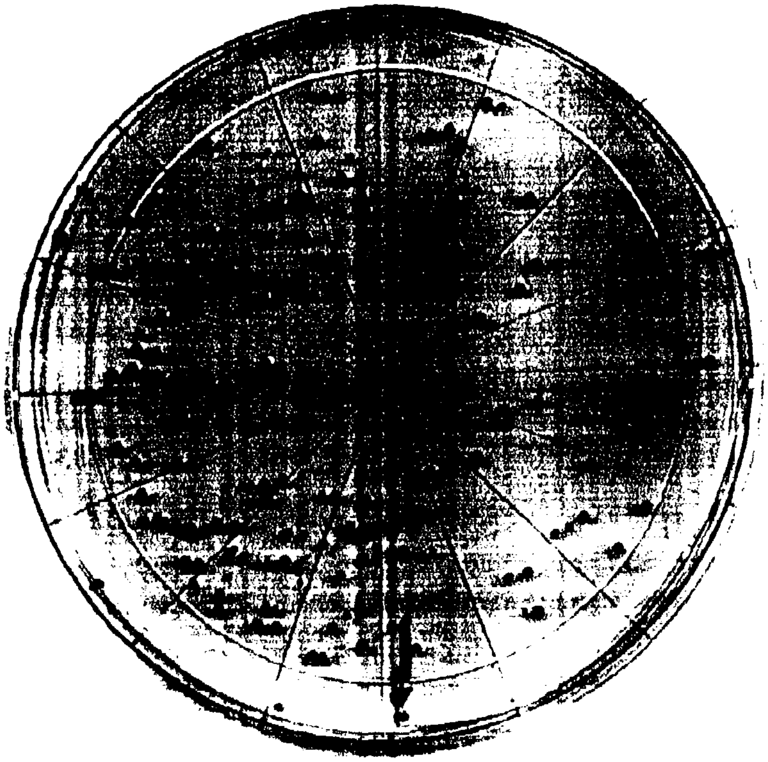

When spores were introduced into the reaction chamber air inlet with the UV/ozone system fully activated (Water on, Ozone On, UV On), the System Inlet plate was overgrown with bacteria. There were about 500 to 600 CFU per sector counted (FIG. 6G), which compared to a significantly lower number of colony forming units, about 15 per sector, that were observed in the System Outlet plate (FIG. 6H). The extent of pathogen neutralization of *Bacillus globigii* spores deliberately introduced in high numbers and passed through the neutralization system in real time, represents about 1-2 orders of magnitude kill or neutralization.

Example 4

Bacteriophage MS2 Virus Neutralization Results

High amounts of airborne Bacteriophage MS2 Virus were continuously introduced into the chamber air inlet of a neutralization system as described in Example 1 under several different sets of conditions set forth below. All experiments were ten minutes long, and air was passed through the system while the system fan was continuously on.

Bacteriophage MS2 Virus does not grow on agar, so an indirect assay was set up to assess the levels of the virus in incoming contaminated air and in outgoing disinfected air. To capture samples of the virus, incoming and outgoing air was bubbled through water and collected continuously during the experiments using the AGI-30 the biosampler. Bacteriophage MS2 is aggressive toward *E. Coli*, causing lysis of the cells that kills them. To assess the amount of bacteriophage MS2 is in incoming contaminated and outgoing disinfected air, sterile agar plates were swabbed with samples collected from the AGI-30 tubes, which were then covered with a suspension of *E. coli* host organism.

Lysis of *E. coli* had to be directly observed visually on the plates, as photographs did not enable accurate counting of lytic plaques. Therefore there are no figures showing the results.

Test 1 Control-(No MS2, All Systems Off-Fan Only), 10-Minute Background

Room air without bacteriophage MS2 was introduced into the chamber air inlet using the nebulizer, and passed through the neutralization system for ten minutes with all systems off-only the fan was on. Aliquots of the samples were taken and swabbed onto sterile agar plates, which were then covered with a suspension of *E. Coli* and incubated at 37 degrees centigrade for twenty hours.

Both System Inlet and System Outlet plates grew confluent lawns of *E. Coli* showing no signs of plaque formation from lytic activity, thus indicating that no bacteriophage was in the incoming or outgoing air.

Test 2 (MS2+/All Systems Off).

Bacteriophage MS2 was introduced as an aerosol into the reaction chamber with the neutralization system off (water off, ozone off and UV off).

After just four hours of incubation at 37 degrees centigrade, both System Inlet and System Outlet plates had confluent lawns of *E. Coli* with readily apparent lytic activity in the form of distinct plaques throughout both plate sets. These results indicate that virus was not lost due to adsorption or desiccation effects inside the test reaction chamber.

After 20 hours incubation at 37° C. the previously clear plaques became hazy due to growth of resistant host cells, but the MS2 exposed plates were still distinctly contaminated with lytic plaques compared to control plates that were not exposed to MS2.

Test 3 (MS2+/All Systems On)

Bacteriophage MS2 was introduced in an aerosol into the neutralization system with the neutralization system fully activated system on (water on, ozone on, UV on). Air Inlet After 20 hours incubation at 37° C., the System inlet plate had confluent lawns of *E. Coli* host organism, with lytic activity that was readily apparent in the form of clear plaques in the lawns. The plaques were hazy due to the growth of resistant *E. coli* host cells, but the plaques were nonetheless distinct. Air Outlet After 20 hours of incubation at 37° C., the System outlet plate had confluent lawns of the *E. Coli* host with no signs of lytic activity. This indicates that 100% of MS2 passing through reaction chamber was inactivated/neutralized after passing through the fully operational neutralization system (water, ozone and UV on) of the present invention.

The results show that the present neutralization system that generates highly active free radicals from the reaction of ozone with water in the presence of UV light, is 100% effective in neutralizing MS2 bacteriophage virus and *Erwinia herbicola* bacteria. While less than completely effective neutralizing *Bacillus globigii* spores (a simulant for Anthrax), the present neutralization system was effective to about 1-2 orders of magnitude kill or neutralization. Variation of the ozone levels, amount of water, intensity of UV and/or the use of a HEPA filter in front of the neutralization system will improve these results.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A pathogen neutralization system, comprising a flow-through reaction chamber having a chamber air inlet located at a first end of the reaction chamber to admit air that is to be disinfected, and a chamber air outlet located at a second end of the reaction chamber to release disinfected air, and defining therebetween a passageway for the passage of air that is to be disinfected through the reaction chamber, the passageway containing no filters and otherwise being substantially free of any obstructions so as not to impede the passage of air through the reaction chamber thereby permitting the neutralization of airborne pathogens in large volumes of ventilated air in real time, wherein the reaction chamber further comprises a. an ozone generator;

b. a water supply line;

c. an ultraviolet light source separate from the ozone generator; and d. a porous matrix for providing increased surface area on which the neutralization of pathogens can occur, wherein the porous matrix consists of metal foam.

2. The pathogen neutralization system as in claim 1, wherein the water supply line is connected to a nozzle to mist water as it is sprayed into the reaction chamber.

3. The pathogen neutralization system as in claim 2, wherein water droplets are sprayed as a mist through the nozzle into the reaction chamber.

4. The pathogen neutralization system of claim 1, wherein the metal is selected from the group comprising aluminum, copper, silver, and oxides thereof.

5. The pathogen neutralization system of claim 1, wherein the metal foam is aluminum foam.

6. The pathogen neutralization system as in claim 1, further comprising a solid support coated with one or more ozone removal catalysts.

7. The pathogen neutralization system as in claim 1, further comprising a microwave generator disposed in the flow-through reaction chamber.

8. The pathogen neutralization system as in claim 1, further comprising an ultrasonic wave generator disposed in the flow-through reaction chamber.

9. The pathogen neutralization system of claim 1, wherein the porous matrix is removable.

10. The pathogen neutralization system of claim 6, wherein the solid support is removable.

11. The pathogen neutralization system as in claim 1, wherein the ozone generator is removable.

12. The pathogen neutralization system as in claim 1, wherein the system is automated with sensors and controllers.

13. The pathogen neutralization system as in claim 1, wherein the ultraviolet light source emits high intensity ultraviolet light.

14. The pathogen neutralization system as in claim 1, wherein the ultraviolet light source emits ultraviolet light having a wavelength in a range from about 100 to about 350 nm.

15. The pathogen neutralization system as in claim 1, wherein the amount of ozone in the flow-through reaction chamber is maintained at a level in a range of from about 0.01 ppm to about 1000 ppm.

16. The pathogen neutralization system as in claim 1, wherein the amount of ozone in the flow-through reaction chamber is maintained at a level in a range from about 0.1 to about 10 ppm.

17. The pathogen neutralization system as in claim 1, wherein the neutralization system is configured for operation in a continuous mode.

18. The pathogen neutralization system as in claim 1, wherein the neutralization system is configured to be activated upon demand.

19. The pathogen neutralization system of claim 6, wherein the ozone removal catalyst is an all-aluminum catalyst.

20. The pathogen neutralization system as in claim 1, wherein the ozone generator is a corona discharge generator.

21. The pathogen neutralization system as in claim 1, further comprising a fan.

22. The pathogen neutralization system as in claim 1, wherein one or more surfactants are added to the water before it is introduced to the reaction chamber.

* * * * *